United States Patent [19]

Musso et al.

[11] Patent Number: 4,835,252

[45] Date of Patent: May 30, 1989

[54] VASOACTIVE INTESTINAL PEPTIDE ANALOGS

[75] Inventors: Gary F. Musso, Encinitas, Calif.; Emil T. Kaiser, New York, N.Y.

[73] Assignee: The Salk Institute Biotechnology/Industrial Associates, Inc., San Diego, Calif.

[21] Appl. No.: 19,148

[22] Filed: Feb. 26, 1987

[51] Int. Cl.$^4$ .............................................. C07K 7/10
[52] U.S. Cl. ..................................................... 530/324
[58] Field of Search ......................................... 530/324

[56] References Cited

U.S. PATENT DOCUMENTS

| | | | |
|---|---|---|---|
| 3,880,826 | 4/1975 | Said et al. | 260/112.5 |
| 4,016,258 | 4/1977 | Said et al. | 260/112.5 |
| 4,605,641 | 8/1986 | Bolin et al. | 260/112.5 |
| 4,734,400 | 3/1988 | Bolin et al. | 514/12 |
| 4,737,487 | 4/1988 | Watts et al. | 514/12 |

FOREIGN PATENT DOCUMENTS

0184309  6/1986  European Pat. Off. .

OTHER PUBLICATIONS

Beyerman et al., "Synthesis, Biological and Immunochemical Properties of Analogues of Secretin and Vasoactive Intestinal Peptide (VIP): The Vasectrins", Life Sciences 29, 895–902 (1981).
Takeyama et al., "Studies on Peptides. XCVII. Synthesis of Porcine Glu$^8$-Vasoactive Intestinal Polypeptide (VIP)," Chem. Pharm. Bull. 28(7), 2265–2269 (1980).
Bodanszky and Natarajan, "Synthesis and Some Pharmacological Properties of the 23-Peptide 15-Lysine-Secretin-(5-27). Special Role of the Residue in Position 15 in Biological Activity of the Vasoactive Intestinal Polypeptide," Journal of Medicinal Chemistry 21, No. 11, 1171–1173 (1978).
Kaiser and Kezdy, "Amphiphilic Secondary Structure: Design of Peptide Hormones," Science 223, 249–255 (1984).
Musso, Ph.D., Dissertation, University of Chicago, Chicago, Ill., U.S.A. (1983).
Robberecht et al., "Effects of HIS Modifications on the Ability of Vasoactive Intestinal Peptide to Stimulate Adenylate Cyclase from Rat and Human Tissues," Peptides 5, 877–881 (1984).
Turner et al., "A Fragment of Vasoactive Intestinal Peptide, VIP (10–28), is an Antagonist of VIP in the Colon Carcinoma Cell Line, HT29," Peptides 7, 849–854 (1986).
James B. D. Palmer et al., "VIP and PHM and Their Role in Nonadrenergic inhibitory Responses in Isolated Airways," *Am. Physiol. Soc.*, pp. 1322–1328, 1986.
Patrick Robberecht et al., "[D-Phe$^4$] Peptide Histidine-Isoleucinamide ([D-Phe$^4$]PHI), a Highly Selective Vasoactive-Intestinal-Peptide (VIP) Agonist, Discriminates VIP-Preferring From Secretin-Preferring Receptors in Rat Pancreatic Membranes," *Eur. J. Biochem.*, 165: 242–249 (1987).
D. McMaster et al., "Iodinated Derivatives of Vasoactive Intestinal Peptide (VIP), PHI and PHM: Purification, Chemical Characterization and Biological Activity," *Peptides*, vol. 8, pp. 663–676, 1987.
Alain Robichon et al., "Chemical Modification of Quanidinium Groups of Vasoactive Intestinal Peptide," *Biochimica et Biophysica Acta*, vol. 923, pp. 250–256, 1987.
R. Dimaline et al., "A Novel Family of VIP-Like Peptides From the Dogfish Scyliorhinus Canicula," *Reg. Peptides*, 18: 356, 1987.

*Primary Examiner*—Delbert R. Phillips
*Assistant Examiner*—Christina Chan
*Attorney, Agent, or Firm*—Fitch, Even, Tabin & Flannery

[57] ABSTRACT

Novel biologically active vasoactive intestinal peptide (VIP) analogues are provided.

12 Claims, No Drawings

VASOACTIVE INTESTINAL PEPTIDE ANALOGS

BACKGROUND OF THE INVENTION

Vasoactive intestinal peptide (hereinafter "VIP") is a known, 28-amino acid, carboxy-terminal -amidated peptide hormone. The sequence of human VIP, which is the same as that of bovine, porcine and rat VIP, is as follows:

H-S-D-A-V-F-T-D-N-Y-T-R-L-R-K-Q-M-A-V-K-K-Y-L-N-S-I-L-N-NH$_2$, wherein the "NH$_2$" at the carboxy-terminus indicates carboxy-terminal amidation.

The presence of VIP has been documented in the neuronal cell structures of the brain, the genitourinary tract, the tracheobronchial tract and the nasal mucosa, the exocrine glands, including salivary, sweat, pancreas and lacrymal glands, the nerve fibers of many peripheral endocrine organs, the peripheral nervous system, and cells of the gastrointestinal tract.

The numerous and varied biological activities associated with VIP include: (1) neuroregulation; (2) inducement of vasodilation; (3) smooth muscle relaxation; (4) stimulation of the intestinal secretion of water and electrolytes; (5) regulation of water and electrolyte transport in various tissues; (6) inhibition of gastric acid secretion; (7) promotion of glycogenesis; and (8) stimulation of the production of pancreatic juice. As a result of its many biological activities, VIP has a number of potential therapeutic uses.

In connection with its mediation of smooth muscle relaxation, VIP can be utilized in reversing broncheal obstruction due to asthmatic bronchospasm. In vitro and in vivo testing have shown VIP to relax tracheal smooth muscle and protect against bronchoconstrictor agents such as histamine and prostaglandin. Wasserman et al. in Vasoactive Intestinal Peptide, ed, S. I. Said, 177-184, Raven Press, N.Y. 1982; Said et al. Ann N.Y. Acad. Sci. 221, 103-117 (1974). Morice et al., Lancet 1983, ii: 1225-1227; Barnes and Dixon, Am. Rev. Resp. Dis. 130, 162-166 (1984); Morice and Sever, Thorax 39, 707 (1984); Altiere and Diamond, J. Appl. Physiol.: Resp. Env. Ex. Physiol. 56, 986-992 (1984); Altiere and Diamond, Br. J. Pharm. 82, 321-328 (1984); Hand et al., Eur. J. Pharm. 98, 279-284 (1984).

VIP causes bronchodilation when administered intravenously or by inhalation. Intravenous administration has drawbacks, in that the VIP is not limited to specific tissues and has a number of effects other than bronchodilation which are usually considered deleterious (i.e. hypotension, tachycardia, flushing). Administration by inhalation is more tissue specific and has fewer side-effects than intravenous administration but appears to less effective than intravenous administration. Altiere et al., Pharmacologist 25, 123 (1983); Bundgaard et al., Eur. J. Respir. Dis. 64 (Suppl. 128), 427-429 (1983); Barnes and Dixon (1984), supra; Altiere et al., Chest 86, 153-154 (1984).

The lower efficacy of VIP in bronchodilation when administered by inhalation, in comparison with administration intravenously, is thought to be caused by either (1) rapid degradation of VIP by compounds, including proteolytic enzymes, present in the respiratory tract both in the bronchial airways and the passageways leading thereto (Barrowcliffe et al., Thorax 41, 88-93 (1986)) or (2) limited absorption of VIP through nasal and pulmonary mucosa, due in part to the size of VIP (about 3300 daltons) (Effros and Mason, Am. Rev. Resp. Dis. 127, S59-S65 (1982); Altiere et al., Chest 86, 153-154 (1984). The net effect of these factors is to prevent VIP from reaching its receptor in lung tissue, as it must in order to have a bronchodilating effect. Hence, there exists a need for biologically active analogs of VIP that, in comparison with native VIP, are more resistant to proteolytic and other forms of degradation and are better able to reach VIP receptors, or capable of binding with greater affinity to VIP receptors.

Reduced susceptibility to proteolysis would be an advantageous property of a VIP analog for another reason as well. Such reduced susceptibility would improve the efficiency of producing the analog by recombinant DNA techniques. Microbial or animal host cells employed in syntheses by recombiannt DNA techniques often contain proteases that degrade heterologous proteins sought to be synthesized by such techniques and thereby reduce the yields of the desired heterologous protein products.

It would also be desirable to have biologically active VIP analogs that are not amidated at the carboxy-terminus. Such analogs would be easier to make, by both recombinant DNA and chemical techniques, than native VIP or other carboxy-terminal-amidated analogs.

Finally, the naturally occurring VIP has so many biological activities that its use is limited, because beneficial effects are associated unavoidably with significant, deleterious side-effects, especially when the VIP is administered intravenously. Thus, it would be desirable to have analogs with effective doses for particular, desirable biological activities of naturally occurring VIP that are decreased relative to the effective doses for other, undesirable activities of the naturally occurring peptide.

Naturally occurring, human VIP and fowl VIP are disclosed in Said et al., U.S. Pat. Nos. 3,880,826 and 4,016,258, respectively. VIP is a member of the secretin family of peptides, which includes, besides VIP, secretin, glucagon, gastric inhibitory peptide, peptide histidine-isoleucine, peptide histidine-methionine, and the amino-terminal 29 amino acids of growth hormone releasing factor. See e.g., Itoh et al., Nature 304, 547-549 (1983).

A number of VIP analogs are known. See, e.g., Bolin et al., U.S. Pat. No. 4, 605, 641; Couvineau et al., Biochem. Biophys. Res. Comm. 121, 493-498 (1984); Beyerman et al., Life Sciences 29, 895-902 (1981); Takeyama et al., Chem. Pharm. Bull. 28, 2265-2269 (1980); Gardner et al., Endocrinol. (Japan.) S. R. No. 1, 1-5 (1980); Bodanszky et al., J. Med. Chem. 21, 1171-1173 (1978); and Bodanszky et al., Proc. Nat. Acad. Sci. (U.S.A.) 70, 382-384 (1973).

Analyses of the secondary structures of certain peptide hormones for amphiphilicity have proven useful in the design of analogs of the hormones which bind, with affinities comparable to the natural hormones, to the specific receptors for the hormones. Kaiser et al., Science 223, 249-255 (1984). Such analyses, and design of analogs based on the analyses, have been carried out for growth hormone releasing factor and glucagon. Musso, Ph.D. Dissertation, University of Chicago, Chicago, Ill. U.S.A. (1983); Kaiser et al., supra. It is recognized, however, that analysis of the secondary structure of a peptide hormone for amphiphilicity, while it might suggest design of analogs that bind with high affinity to the harmone's receptors, is not useful in predicting other properties of the hormones, including, most importantly, biological activity and potency, which depend on numerous, ill understood factors besides receptor affinity.

SUMMARY OF THE INVENTION

The secondary structure of naturally occurring, human VIP has been analyzed for amphiphilicity. It has been discovered that residues 6–28 of the VIP can be arranged into a pi-helix in which half of the molecule has uncharged polar or charged amino acids and the other half, with two exceptions, has hydrophobic amino acids. The two exceptions are the uncharged polar Asn at position 9 and the charged Arg at position 14, on the side of the molecule which, in the pi-helical form, is otherwise hydrophobic.

Starting with the discovery of the amphiphilic secondary structure of the naturally occurring VIP, novel analogs of VIP have been discovered, which have one or more of the biological activities characteristic of the naturally occurring peptide.

DETAILED DESCRIPTION OF THE INVENTION

The present invention entails novel, biologically active analogs of vasoactive intestinal peptide with the formula: H-S-D-A-V-$X_{21}$-D-$X_{22}$-$X_{12}$-$X_{23}$-$X_{31}$-$X_{41}$-R-$X_{32}$-$X_{33}$-$X_{51}$-A-$X_{52}$-$X_{34}$-$X_{35}$-$X_{13}$-$X_{53}$-$X_{24}$-$X_{25}$-$X_{55}$-$X_{56}$-$X_{26}$-(NH$_2$)$_i$, wherein $X_{11}$, $X_{12}$, and $X_{13}$ are the same or different are each selected from the group consisting of F or Y; $X_{21}$, $X_{22}$, $X_{23}$, $X_{24}$, $X_{25}$, and $X_{26}$ are the same or different and are each selected from the group consisting of T, S, Q, N, and A; $X_{31}$, $X_{32}$, $X_{33}$, $X_{34}$, and $X_{35}$ are the same or different and are each selected from the group consisting of R, K, S, and Q; $X_{41}$ is selected from the group consisting of L, M, V, I, F, and Y; $X_{51}$, $X_{52}$, $X_{53}$, and $X_{55}$ are the same or different and are each selected from the group consisting of L, M, I, and V; and $X_{56}$ is selected from the group consisting of L and V; and wherein i is 0 or 1, wherein 0 indicates the peptide is not carboxy-terminal-amidated and 1 indicates that the peptide is carboxy-terminal-amidated.

Preferred among these analogs are those of the following sequences:

Analog I: H-S-D-A-V-Y-S-D-S-F-S-R-Y-R-R-S-V-A-L-R-R-F-V-S-N-V-V-T-(NH$_2$)$_i$;
Analog II: H-S-D-A-V-Y-S-D-S-F-S-R-Y-R-S-R-V-A-L-S-R-F-V-R-N-V-V-T-(NH$_2$)$_i$;
Analog III: H-S-D-A-V-Y-S-D-S-F-R-S-Y-R-S-R-V-A-L-S-R-F-V-R-N-V-V-T-(NH$_2$)$_i$;
Analog IV: H-S-D-A-V-Y-T-D-N-F-S-R-Y-R-K-Q-V-A-L-K-K-F-V-N-S-V-V-T-(NH$_2$)$_i$;
Analog V: H-S-D-A-V-F-S-D-S-Y-S-R-F-R-R-S-M-A-V-R-R-Y-L-S-N-V-L-T-(NH$_2$)$_i$;
Analog VI: H-S-D-A-V-Y-S-D-S-F-S-R-F-R-K-Q-M-A-V-K-K-Y-L-N-S-V-L-T-(NH$_2$)$_i$;
Analog VII: H-S-D-A-V-F-T-D-N-Y-S-R-Y-R-R-Q-M-A-V-K-K-Y-L-N-S-V-L-T-(NH$_2$)$_i$;
Analog VIII: H-S-D-A-V-F-T-D-N-Y-S-R-F-R-K-S-V-A-V-K-K-Y-L-N-S-V-L-T-(NH$_2$)$_i$;
Analog IX: H-S-D-A-V-F-T-D-N-Y-S-R-F-R-K-Q-M-A-V-R-R-F-V-N-S-V-L-T-(NH$_2$)$_i$;
Analog X: H-S-D-A-V-F-T-D-N-Y-S-R-F-R-K-Q-M-A-V-K-K-Y-L-S-N-V-V-T-(NH$_2$)$_i$;

Most preferred is carboxy-terminal-amidated Analog V.

It is intended that an analog is also within the scope of the present invention if it is essentially equivalent to an analog of the invention, as specified above. An analog is essentially equivalent to one specified above if it has one or more of the biological activities characteristic of human VIP, has the same number of amino acids as the specified analog and, in comparison with the sequence of the specified analog, has at most five amino acid substitutions, all of which would be considered neutral in the art (i.e., acidic for acidic, basic for basic, uncharged polar for uncharged polar, hydrophobic for hydrophobic, and the like).

The acidic amino acids are Asp and Glu. The basic amino acids are Arg, Lys, and His. The hydrophobic amino acids are Ala, Ile, Leu, Met, Phe, Trp, Tyr, and Val. Uncharged polar amino acids are Asn, Gln, Ser, and Thr. Gly can be substituted for an uncharged polar or a hydrophobic amino acid, but substitutions with Gly are avoided because helical structures may be destabilized by such a substitution. Substitutions with Pro are generally avoided because of a significant effect on secondary structure of inserting a Pro in place of another amino acid. Substitutions with Cys are generally avoided because of the reactivity of the sulfhydryl group.

The amino acids of the VIP analogs of the invention have the L configuration. The amino acids are identified according to the following three-letter or one-letter abbreviations:

| Amino Acid | Three-Letter Abbreviation | One-Letter Abbreviation |
|---|---|---|
| L-Alanine | Ala | A |
| L-Arginine | Arg | R |
| L-Asparagine | Asn | N |
| L-Aspartic Acid | Asp | D |
| L-Cysteine | Cys | C |
| L-Glutamine | Gln | Q |
| L-Glutamic Acid | Glu | E |
| L-Glycine | Gly | G |
| L-Histidine | His | H |
| L-Isoleucine | Ile | I |
| L-Leucine | Leu | L |
| L-Lysine | Lys | K |
| L-Methionine | Met | M |
| L-Phenylalanine | Phe | F |
| L-Proline | Pro | P |
| L-Serine | Ser | S |
| L-Threonine | Thr | T |
| L-Tryptophan | Trp | W |
| L-Tyrosine | Tyr | Y |
| L-Valine | Val | V |

"Asx" means Asp or Asn.
"Glx" means Glu or Gln.

An analog of the present invention can be made by exclusively solid phase techniques, by partial solid-phase techniques, by fragment condensation, by classical solution coupling, or or by employing recombinant DNA techniques with bacteria, such as E. coli or B. subtilis; yeast, such as S. cerevisiae or P. pastoris; or mammalian cells.

Methods of making a polypeptide of known sequence by recombinant DNA techniques are well known in the art. See, e.g., U.S. Pat. No. 4689,318 which is and incorporated herein by reference. Methods for amidating at the carboxy-terminus peptides that have been made by recombinant DNA techniques are also know. See, e.g., European Patent Application Publication No. 0133282.

Methods for chemical synthesis of polypeptides are also well known in the art and, in this regard, reference is made, by way of illustration, to the following literature: R. A. Houghten, Proc. Natl. Acad. Sci. (U.S.A.) 82, 5131–5135 (1985); Yamashino and Li, J. Am. Chem. Soc. 100, 5174–5178 (1978); Stewart and Young, Solid Phase Peptide Synthesis (W. H. Freeman and Co. 1969); Brown, et al., J. C. S. Perkin I, 1983, 1161–1167; M. Bodanszky, et al., Bioorg. Chem. 3, 320–323 (1974); E. Atherton, et al., J. C. S. Perkin I, 1981, 538–546; S. R. Pettitt, Synthetic Peptides, (Elsevier Scientific Publishing Co. 1976); Y. S. Klausner and Bodanszky, Bioorg. Chem. 2, 354–362 (1973); U.S. Pat. Nos. 4,632,211; 4,237,046; 4,105,603; 3,842,067; 3,862,925; and 4,689,318 all incorporated herein by reference.

Preferred, automated, step-wise solid-phase methods for synthesis of peptides of the invention are provided in the examples below.

The VIP analogs encompassed by the present invention have one or more of the biological activities of naturally occurring VIP, as described above, and, as such, are useful therapeutically in one or more of the ways in which VIP is known to be useful, e.g., to relieve bronchoconstriction in a mammal suffering from asthma or exposed to an untoward amount of a bronchoconstrictor such as histamine or a prostaglandin; to reduce blood pressure in a mammal suffering from hypertension; or to inhibit gastric acid secretion in a mammal suffering from a disease, such as ulcers, due to or exacerbated by excessive gastric acid secretion.

The biological activity of an analog of the invention is determined by comparing the analog with naturally occurring VIP in a lung-strip assay for VIP-induced muscle relaxation (Saga and Said, Trans. Assoc. Am. Physicians 7, 304–310 (1984)) or an assay for stimulation of amylase secretion from rat pancreatic acinar cells. Other important properties of analogs of the invention are determined by a radioreceptor assay for binding of the analog to VIP-receptor in rat lung membrane, and an homogenized rat lung assay for evaluating the resistance of an analog to proteolytic degradation.

Data for analogs of the invention from various assays are presented in the examples below.

The analogs of the invention are employed therapeutically, under the guidance of a physician, to reduce hypertension in a person suffering therefrom or to reduce bronchoconstriction in a person suffering from asthma or exposed to an untoward, bronchoconstricting concentration of a bronchoconstrictor such as histamine or a prostaglandin.

The preferred use of the analogs of the invention is in relieving bronchoconstriction due to asthma in persons suffering therefrom.

The dose and dosage regimen of an analog according to the invention that is suitable for administration to a particular patient can be readily determined by a physician considering the patient's age, sex, weight, general medical condition, and specific condition and severity thereof for which the analog is being administered; the route of administration of the analog; the pharmaceutical carrier with which the analog may be combined; and the analog's biological activity, affinity for receptor and rate of proteolytic degradation, relative to that of naturally occurring human VIP, in the above-described assays.

Generally, intravenous injection of 0.1–10 ug of analog/kg body weight, by bolus injection or by infusion over a period of about 5 minutes to about 60 minutes, is sufficient to reduce hypertension or relieve bronchoconstriction. Aerosol inhalation of 1–100 ug of analog/kg body weight is also sufficient for relief of bronchoconstriction.

Intravenous administration, by bolus injection or continuous infusion, is preferred for use of the analogs of the invention in treatment of hypertension.

For use of the analogs in relieving bronchoconstriction, administration intranasally by inhalation of an aerosol containing an analog of the invention is preferred.

The analogs of the invention, or a pharmaceutically acceptable salt thereof, can be combined, over a wide concentration range (e.g., 0.001 to 1.0 wt %) with any standard pharmaceutical carrier (e.g., physiological saline, THAM solution, or the like) to facilitate administration by any of various routes including intravenous, subcutaneous, intramuscular, oral, or intranasal, including by inhalation.

Pharmaceutically acceptable acid addition salts of the analogs of the invention can be prepared with any of a variety of inorganic or organic acids, such as, for example, sulfuric, phosphoric, hydrochloric, hydrobromic, nitric, citric, succinic, acetic, benzoic and ascorbic.

The invention will now be illustrated in greater detail in the following examples.

EXAMPLE I

Preparation of VIP Analogs

Peptides were synthesized using solid-phase methodology, generally described by Merrifield (J. Amer. Chem. Soc., 85, 2149 (1963)) (see also Stewart and Young, supra.) with various modifications described herein, carried out on a Beckman 990B automated peptide synthesizer (Beckman Instruments, Inc., Fullerton, Calif., U.S.A.).

Sequential assembly of a peptide analog is conducted from the carboxy-terminus, bonded to a solid-phase resin, to the amino terminus; the addition of amino acids to a peptide chain is automated after the attachment of the carboxy-terminal amino acid to the resin.

For peptides that will have a carboxyl group at the carboxy-terminus, p-chloromethyl-derivatized polystyrene supports are employed, and the carboxy-terminal amino acid is esterified to the support via reaction with KF as described by Horiki, et al., Chem Lett. 1978, 165–168. For peptides which are amidated at the carboxy-terminus, p-methylbenzhydryl-amine-derivatized polystyrene supports are employed, and the carboxy-terminal amino acid is attached to the support via dicyclohexylcarbodiimide-mediated coupling followed by acetylation of the unreacted amine sites on the support with acetyl imidazole. Following attachment of the carboxy-terminal amino acid to the support, the level of substitution of the amino acid on the support is determined by the picric acid titration method described by Gisin, Anal. Chim. Acta, 58, 248–249 (1972). Substitution levels for automated syntheses are preferably between 0.2 and 0.6 mmol amino acid per g resin. A typical synthesis is performed on a scale of 0.25–0.5 mmol, and thus is initiated with 0.4–2.5 g amino acid-derivatized resin. Steps in the syntheses of the VIP analogs employed the following protocol:

| STEP | REAGENT | MIX TIME (MIN) | # OF TIMES |
|---|---|---|---|
| 1 | Methylene Chloride | 0.5 | 4 |
| 2 | 50% TFA/Methylene Chloride/ | 1 | 1 |

| STEP | REAGENT | MIX TIME (MIN) | # OF TIMES |
|------|---------|----------------|------------|
|   | 1% Ethanedithiol |   |   |
| 3 | 50% TFA/Methylene Chloride/ 1% Ethanedithiol | 20 | 1 |
| 4 | Methylene Chloride | 1 | 3 |
| 5 | Isopropanol | 1 | 2 |
| 6 | Methylene Chloride | 1 | 2 |
| 7 | 5% DIEA/Methylene Chloride | 2 | 2 |
| 8 | Methylene Chloride | 1 | 1 |
| 9 | 5% DIEA/Methylene Chloride | 2 | 2 |
| 10 | Methylene Chloride | 1 | 3 |
| 11 | Amino Acid | Variable | 1 |
| 12 | Methylene Chloride | 1 | 2 |
| 13 | Dimethylformamide | 1 | 2 |
| 14 | 33% Methanol/Methylene Chloride | 1 | 2 |
| 15 | Stop or Return for Next Coupling |   |   |

Methylene chloride, dimethylformamide (DMF), and isopropanol were reagent grade and stored over 4 A molecular sieves. Ethanedithiol, hydroxybenzotrazole (HOBT), and diisopropylethylamine (DIEA) were used as purchased from Aldrich Chemical Company (Milwaukee, Wis., U.S.A.). Trifluoroacetic acid (TFA) was freshly distilled prior to use. Dicyclohexylcarbodiimide (DCC) was distilled in vacuo. The coupling of amino acids was usually carried out for 30 minutes with the preformed symmetric anhydride of the amino acid involved (see Yamashino and Li, supra.) with at least a 3-fold excess of symmetric anhydride with respect to the available amine sites on the resin. Arginine was coupled with DCC using 3.5-fold excess arginine and 3-fold excess DCC in 25% DMF/methylene chloride for 2 hours. Asparagine and glutamine were also dissolved in 25% DMF/methylene chloride and coupled as HOBT-active esters for 2 hours.

The tert-butyloxycarbonyl (BOC) group was used for protection of the alpha amine group of all amino acids employed in the syntheses; however, other protecting groups known in the art for alpha amines can be employed successfully. Side-chain functionalities were protected as follows: Arg and His with p-toluene-sulfonyl; Asp, Glu, Ser, and Thr with benzyl; Lys with 2-chlorobenzyloxycarbonyl; and Tyr with 2, 6-dichlorobenzyl. The resins employed in the syntheses were, for the carboxy-terminated analogs, chloromethyl-derivatized polystyrene-1% divinylbenzene (200–400 mesh) from U.S. Biochemicals Corp., Cleveland, Ohio, U.S.A. (1.1 milliequivalent Cl/g resin) or, for carboxy-terminal-amidated analogs, p-methylbenzhydrylamine-derivatized polystyrene-1% divinylbenzene (150–200 mesh) from Colorado Biotechnology Associates (Boulder, Colorado, U.S.A.) (0.45 milliequivalent $NH_2$/g resin).

After assembly of the completed analog, the amino-terminal BOC group is removed using steps 1–9 of the above protocol and then the resin is washed with methanol and dried. The analogs are then deprotected and removed from the resin support by treatment with HF/anisole for 1 hour at 0° C. Following removal of the HF, the crude analog preparation was washed with 3 portions of ethyl acetate, extracted with 3 portions of 10% acetic acid in water, and then lyophilized.

The resulting crude preparations were purified by preparative high performance liquid chromatography (HPLC) on a Zorbax C-8 column (21×250 mm) (DuPont Co., Wilmington, Delaware U.S.A.). Preparative HPLC separations were performed with the Zorbax column on a Waters Delta Prep System (Millipor Corp., Milford, Mass., U.S.A.) at a flow rate of 15 ml/min. Samples were introduced in 50–250 portions in 0.1% TFA (running buffer) and eluted from the column with an acetonitrile gradient (20–40%/40 minutes). Peptide fractions were monitored by UV Absorbance at 230 nm. In all cases, fractions were manually collected at peak detection and subsequently lyophilized. The purified fractions were reanalyzed on an analytical HPLC (Beckman System 345, Beckman Instruments, Inc.) using an Altex C-18 column (4.6×250 mm) (Beckman Instruments, Inc.) using a buffer system of 0.1% phosphoric acid, 0.1 M sodium perchlorate, pH 2.5 and an acetonitrile gradient. A 10%–60% acetonitrile gradient over 50 minutes was used to elute the peptide components. A portion of the fractions which appeared homogenous was removed and hydrolyzed for amino acid analysis. The analogs with the correct amino acid composition were then subjected to bioassay.

For amino acid analysis, a sample of analog was hydrolyzed in 6 N HCl containing 1% phenol for 24 hours at 110° C. Analyses were performed on a Beckman 6300 Amino Acid-Analyser (Beckman Instruments, Inc.) interfaced with a Nelson 3000 Data System (Nelson Analytical, Inc., Cupertino, Calif., U.S.A.).

(a) Preparation of BOC-Thr(OBz)-Resin

A typical preparation of peptide resin containing threonine, protected with benzyl at the hydroxyl oxygen, as the C-terminal amino acid, is illustrated in the following example: A 10 g portion of p-methylbenzhydrylamine resin (150–200 mesh, 1% crosslinked, 0.45 meq/g (Colorado Biotechnology Associates, Inc.) was first swelled in 100 ml of methylene chloride. The support, received as the hydrochloride salt, was then neutralized by treatment with 5% DIEA in methylene chloride (2×100 ml for 2 min.). It was washed two more times in methylene chloride. A solution of 1.55 g BOC-Thr(OBz) and 1.03 g DCC in 75 ml of methylene chloride was added to the resin and the mixture was stirred for 2 hours, filtered and washed with methanol (3×75 ml). The resin was then dried overnight in vacuo. The loading of BOC-Thr(OBz) on the resin support was determined by the picric acid titration method described by Gisin, supra. Substitution was determined to be 0.475 mmol/g. The resin was then treated with 550 mg of acetylimidazole in 50 ml of methylene chloride containing 50 ul of triethylamine in order to cap any unreacted amine site on the support.

(b) Syntheses of the Carboxy-Terminal-Amidated VIP Analog I

The synthesis of Analog I: H-S-D-A-V-Y-S-D-S-F-S-R-Y-R-R-S-V-A-L-R -R-F-V-S-N-V-V-T-($NH_2$), amidated at the carboxy-terminus, was initiated by using 475 mg of a BOC-Thr(OBz) resin (substitution level=0.527 mmol/g), prepared following the procedure of Example I(a). All solvents in the automated protocol were metered in 20 ml portions per addition. For couplings requiring symmetric anhydrides, the acylating component was preformed 10 minutes prior to addition by dissolving 6.5-fold excess amino acid with 3-fold excess DCC in 20 ml methylene chloride at 0° C. The resulting dicyclohexylurea was filtered off and the activated component was added to the reaction vessel of the synthesizer. Couplings of Arg, Asn and Gln were done without preactivation and used 15 ml of methylene chloride and 5 ml of DMF. The amount of components is summarized on the following table:

| CYCLE # | GRAMS OF PROTECTED AMINO ACID | CYCLE # | GRAMS OF PROTECTED AMINO ACID |
|---|---|---|---|
| 1 | 0.353 V | 2 | 0.353 V |
| 3 | 0.261 N, 0.135 HOBT | 4 | 0.479 S |
| 5 | 0.353 V | 6 | 0.430 F |
| 7 | 0.375 R | 8 | 0.374 R |
| 9 | 0.404 L | 10 | 0.307 A |
| 11 | 0.353 V | 12 | 0.479 S |
| 13 | 0.374 R | 14 | 0.374 R |
| 15 | 0.715 Y | 16 | 0.374 R |
| 17 | 0.479 S | 18 | 0.430 F |
| 19 | 0.479 S | 20 | 0.546 D |
| 21 | 0.479 S | 22 | 0.715 Y |
| 23 | 0.353 V | 24 | 0.307 A |
| 25 | 0.546 D | 26 | 0.479 S |
| 27 | 0.796 H | | |

Upon completion of the synthesis, 1.61 g of peptide-resin was obtained. To this was added 2 ml of anisole in an HF reaction vessel and 15 ml of HF was distilled in at −78° C. After 1 hour at 0° C., the HF was removed under vacuum, and the peptide was washed and extracted to yield 725 mg of crude peptide. A 250 mg portion was dissolved in 5 ml of 0.1% TFA containing 20% acetonitrile and injected on the preparative HPCL using the previously described conditions. The sizable peaks were collected and lyophilized. An aliquot of each fraction was reanalyzed by analytical HPLC and also hydrolyzed for amino acid analysis. One fraction was homogeneous and gave proper amino acid analysis yielding 6.5 mg of peptide. Amino acid analysis results: Asx (3)3.6, Thr (1)0.7, Ser (6)5.4, Ala (2)2.0, Val (5)5.1, Leu (1)1.0, Tyr (2)2.0, Phe (2)2.2, His (1)0.8, Arg (5)4.9.

Synthesis of the Carboxy-Terminal-Amidated VIP Analog V

The synthesis of Analog V: H-S-D-A-V-F-S-D-S-Y-S-R-F-R-R-M-A-V-R-R -Y-L-S-N-V-L-T-(NH$_2$), amidated at the carboxy-terminus, was initiated with 1.31 g of a BOC-Thr(OBz) resin (sub. level 0.38 mmol/g; 0.5 mmol scale) prepared following the procedure described in Example I(a). Coupling of sequential amino acids is detailed as follows:

| CYCLE # | GRAMS OF PROTECTED AMINO ACID | CYCLE # | GRAMS OF PROTECTED AMINO ACID |
|---|---|---|---|
| 1 | 0.695 L | 2 | 0.625 V |
| 3 | 0.697 N, 0.338 HOBT | 4 | 0.883 S |
| 5 | 0.694 L | 6 | 1.43 Y |
| 7 | 1.285 R | 8 | 1.285 R |
| 9 | 0.652 V | 10 | 0.568 A |
| 11 | 0.748 M | 12 | 0.883 S |
| 13 | 1.285 R | 14 | 1.285 R |
| 15 | 0.796 F | 16 | 1.285 R |
| 17 | 0.883 S | 18 | 1.43 Y |
| 19 | 0.883 S | 20 | 0.970 D |
| 21 | 0.883 S | 22 | 0.796 F |
| 23 | 0.652 V | 24 | 0.568 A |
| 25 | 0.970 D | 26 | 0.883 S |
| 27 | 1.471 H | | |

Yield of the dried peptide resin mixture was 3.39 g. A 1.7 g portion of this was cleaved by the two step HF procedure described by Tam et al., J. Amer. Chem. Soc., 105, 6442–6455 (1983). To the resin was added 3 ml of p-cresol and 19.5 ml dimethylsulfide (DMS). The deprotection was initiated by the addition of 7.5 ml of HF and the reaction mixture was stirred at 0° C. for 2 hours. Following removal of HF and DMS, the resin was washed with ethylacetate and dried. To the crude resin-peptide mix was added 2 ml p-cresol and 18 ml of HF. After stirring for 1 hour at 0° C., the reaction was worked up as in example I(b). The crude extracted peptide was immediately applied to a Sephadex G-15 column and eluted with 10% acetic acid. The initial major peak was pooled and lyophilized to yield 695 mg of crude peptide. 150 mg of this was purified by preparative HPLC, as described for Analog I, yielding 4.2 mg of purified Analog V with its proper amino acid composition. Amino acid analysis results were as follows: Asx(3) 2.8, Thr(1) 1.3, Ser(6) 4.4, Ala(2) 1.9, Val(3) 3.0, Met(1) 1.1, Leu(2) 2.4, Tyr(2) 2.3, Phe(2) 1.8, His(1) 0.6, Arg(5) 5.8.

(b) Syntheses of the Carboxy-Terminal-Amidated VIP Analog II–IV and VI–X

Carboxy-terminal-amidated analogs II–IV and VI–X were synthesized and purified in substantially the same manner as described above for Analogs I and V, beginning with BOC-Thr(OBz)-derivatized p-methylbenzhydrylamine resin, described above in Example I(a), and employing the appropriate protected amino acid in each cycle of the automated synthesis.

EXAMPLE II

Radioreceptor Assays of Affinities of Analogs for VIP Receptor

Radioreceptor assays were carried out to determine the affinities of analogs of Example I for VIP receptors in rat lung membrane, following Leroux et al., Endocrinology 114, 1506–1512 (1984).

The following buffers were prepared:
Buffer A: 250 mM sucrose, 5 mM MgCl$_2$, 25 mM Tris, pH 7.4
Buffer B: 5 mM MgCl$_2$, 25 mM Tris, pH 7.4
Buffer C: 25 mM Tris, 5 mM MgCl$_2$, 1 mg/ml bacitracin, 2 mg/ml bovine serum albumin ("BSA"), pH 7.4
Phenylmethylsulfonyl fluoride ("PMSF") was added, to a final concentration of 1 mM, to the buffers immediately prior to their use.

Naturally occurring human VIP, human VIP not amidated at the carboxy-terminus, chicken VIP, and guinea pig VIP were synthesized as described in Example I. (Human VIP so synthesized was indistinguishable from that purchased from Peninsula Labs, Inc. (Belmont, California, U.S.A.).) Stock solutions of $2.5 \times 10^{-5}$M of the VIP's in $10^{-2}$M acetic acid, 1 mg/ml BSA, and 50 mg/l ascorbic acid were prepared and, for assays, diluted, to appropriate concentrations described below, with Buffer C.

$^{125}$I-labeled, human· VIP ($^{125}$I-VIP) was purchased from New England Nuclear (Boston, Mass., U.S.A.). The peptide as purchased was diluted to $10^{-5}$ Ci/ml with Buffer C and stored in 25 ul or 50 ul aliquots at −20° C., which were subsequently diluted with Buffer C, as described below, for the assays.

Rat lung membrane was prepared for the assay as follows, following Leroux et al., supra: Five female Sprague-Dawley rats (200–250 g) were sacrificed and their hearts perfused with iced, phosphate-buffered saline (PBS) through the right atrium (approximately 30 ml PBS per rat). The lungs, which were whitened, were then removed and placed directly in iced PBS and any blood was rinsed from the tissue. The lung tissue was then transferred to a weighing device on ice; blood vessels, fat and the like were removed from the tissue; and the tissue was blotted and weighed. The lung tissue was then transferred to a 50 cm$^3$ Falcon tube with 2 ml of Buffer A per g lung tissue (approximately 25 ml Buffer A) and homogenized at 4° C. 1 minute in a polytron (Brinkmann Instruments Co., Westbury, N.Y., U.S.A.) and then with a glass/teflon homogenizer (approximately 5-6 strokes). The homogenate was filtered through two layers of cheesecloth, and the filtrate was then transferred to tubes for centrifugation at 30,000×g for 10 minutes. The pellets were then resuspended in approximately 70 ml of Buffer B using a glass/teflon homogenizer and the resulting suspensions were again centrifuged at 30,000×g for ten minutes. The resulting pellets were resuspended in 50 ml of Buffer B using a glass/teflon homogenizer. The suspension was divided into 1.0 ml aliquots in microfuge tubes, which were quickly frozen and stored on dry ice until use.

When used, an aliquot of suspension was thawed and microfuged at 4° C. for several minutes to pellet suspended material. The supernatant was carefully removed and the pellet resuspended in 1 ml of Buffer C. Protein concentrations (determined by the Lowry method) of the final suspension were 3.0–3.2 mg/ml.

Prior to use of a VIP receptor-containing suspension in an assay, the protein concentration was adjusted to 2 mg/ml by addition of Buffer C. Then 100 ul of this suspension (2 mg/ml) was combined with 100 ul of solution of $^{125}$I-VIP, 100 ul of solution of the VIP or analog thereof being assayed and 200 ul of Buffer C; consequently, the concentration of protein from the rat lung VIP receptor preparations used in the assays was 0.4 mg/ml.

In the radioreceptor assays, the ability of analog to displace $^{125}$I-VIP from binding in the receptor preparation was measured by a standard procedure. For each analog, and naturally occurring human VIP as standard, a series of solutions, of 500 ul total volume in Buffer C, containing various concentrations of analog or standard (between about $10^{-11}$ M and $10^{-6}$ M), $^{125}$I-VIP at 100 cpm/ul (about $2\times10^{-10}$ M), and receptor preparation (0.4 mg protein/ml) were assayed. Each solution was prepared by first combining a solution (100 ul) of analog or standard in Buffer C and a solution in Buffer C of $^{125}$I-VIP (100 ul) with 200 ul Buffer C, then adding receptor suspension (100 ul) (2 mg protein/ml in Buffer C) and incubating for 20 minutes at 37° C. After the incubation, the solutions were chilled on ice and then combined with 2 ml of ice-cold Buffer C. The resulting solutions were then centrifuged at 4° C. at 2500×g for 30 minutes. The supernatant was discarded and the pellet counted by a standard technique. All solutions were run in duplicate.

Non-specific binding of $^{125}$I-VIP was determined from a run with $5\times10^{-7}$ M human VIP, far in excess of the approximately $5\times10^{-10}$ M required to occupy half the receptor sites in a rat lung membrane receptor preparation at 0.4 mg protein/ml. Total counts (bound plus unbound) was determined by carrying out an assay without membrane preparation and counting the final solution. Total binding of $^{125}$I-VIP was measured by carrying out the assay with $^{125}$I-VIP but without analog or standard. The linear range of the assay was $10^{-10}$ M to $10^{-8}$ M.

The assays yielded a value, termed herein "relative IC$_{50}$", for each analog, which is the concentration of the analog required to displace $^{125}$I-VIP from half of the receptor sites in an assay mixture divided by the concentration of standard (i.e., human VIP) required to displace $^{125}$I-VIP from half of the receptor sites in the same assay mixture. In the assays described herein, human VIP at a concentration of about $5\times10^{-10}$ M was required to displace half of the $^{125}$I-VIP.

Results of the assays were as follows:

| ANALOG | RELATIVE IC$_{50}$ |
| --- | --- |
| Human VIP | 1.00 |
| Human VIP, non-amidated at carboxy-terminus | 6.2 |
| Chicken VIP | 1.4 |
| Guinea Pig VIP | 20 |
| I | 140 |
| II | 550 |
| III | 2350 |
| IV | 1040 |
| V | 4.2 |
| VII | 86 |
| IX | 175 |

EXAMPLE III

Bioactivity Assay of VIP Analogs

The bioactivity of analogs of Example I, chicken VIP, guinea pig VIP, and human VIP without amidation at the carboxy-terminus was determined, relative to that of naturally occurring human VIP, by an amylase-release assay employing dispersed guinea pig pancreatic acinar cells. The assay was essentially that described by Peikin et al., Am. J. Physiol. 235, E743–E749 (1978).

For the assays conducted each day, dispersed acinar cells, free of debris, were freshly prepared from a pancreas of a male or female guinea pig (120–150 gm), following generally the method described by Peikin et al., supra.

The procedure employed a "standard incubation medium," which consisted of 95 mM NaCl; 6 mM KCl; 2.5 mM NaH$_2$PO$_4$; 5 mM each of sodium pyruvate, sodium fumarate and sodium glutamate; 0.5 mM CaCl$_2$, 1.0 mM MgCl$_2$, 11.5 mM glucose, 0.05 mg/ml glutamine; amino acids and vitamins from Eagle's Minimum Essential Medium at their concentration in such Eagle's Medium; 25 mM HEPES; 0.08 mg/ml soybean trypsin inhibitor (Calbiochem); pH 7.4.

The animal was sacrificed, its pancreas removed and the pancreas trimmed of fat, blood vessels, duodenum and the like. With a syringe with a 25 gauge needle, 10.0 ml of collagenase solution (standard incubation medium with 0.2 mg/ml C. histolyticum collagenase and 2 mg/ml BSA (Fraction V) (both from Calbiochem, San Diego, California, U.S.A.)) was injected into the pancreas, which was then transferred to a 25 ml flask, gassed with 100% O$_2$, and shaken on a shaker as rapidly as possible for 10 minutes at 37° C. Then the liquid was poured off and replaced with another 5.0 ml of collagenase solution, and the gassing with 100% O$_2$ and shaking for 10 minutes at 37° C. were repeated. The replacement of liquid, gassing with 100% O$_2$ and shaking at 37° C. were again repeated. If, by visual inspection, digestion appeared to be incomplete, vigorous shaking by hand with 1 minute incubation at 37° C. were repeated until digestion was complete. The mass was then broken up further by passing chunks through a large bore serological pipette, and then a small bore pipette. Very large chunks, fur and debris were removed with a long Pasteur pipette. Then half of the resulting acinar cell suspension was placed into each of two 15 ml clear, polystyrene tubes, each containing 4.0 ml of 4.0% BSA solution (standard incubation medium with 40 mg/ml BSA (Fraction V) and 2 mM, rather than 0.5 mM, CaCl$_2$). Both combinations were mixed thoroughly and debris was again removed. The resulting suspensions were spun at medium speed in a tabletop centrifuge for 30 seconds, the supernatants were discarded, and the pellets were resuspended in 4.0 ml of 4.0% BSA and 4.0 ml of 0.2% BSA solution (standard suspension medium with 2 mg/ml BSA (Fraction V) and 2 mM, rather than 0.5 mM, CaCl$_2$), the suspension was again cleaned of debris, and then spun as above with the tabletop centrifuge. The supernatants were discarded and the pellets again washed with 4.0 ml of 4% BSA solution and repelleted as above with the tabletop centrifuge. Again, the supernatants were discarded and the pellets were carried into one 250 ml Erlenmeyer flask, to which 50.0 ml of 1% BSA solution (standard incubation medium with 10 mg/ml BSA (Fraction V) and 5 mM theophylline) had been added. When the cells were not used immediately, the suspension was gassed with 100% O$_2$. The preparation was acceptable for use in an assay only if the cells were fine and well dispersed and there was nothing visible in the preparation other than cells.

VIP analog to be assayed was dissolved in 1% BSA solutions at concentrations of $10^{-5}$M, $10^{-6}$M, $10^{-7}$M, $10^{-8}$M and $10^{-9}$M. Suitable volumes of these solutions were then combined with 500 ul of the acinar cell suspension so that duplicate samples of each of the following concentrations of analog in the suspensions resulted: 0 (control, 500 ul acinar cell suspension, no VIP); $10^{-11}$M; $10^{-10}$M; $3\times10^{-10}$M; $10^{-9}$M; $3\times10^{-9}$M; $10^{-8}$M; and $10^{-7}$M. The resulting suspensions were incubated for 30 minutes at 37° C.; no gassing or capping was employed.

The "O" time point amylase release values were obtained by spinning, at high speed in a refrigerated tabletop centrifuge for 30 seconds, two samples, each of 400 ul of unincubated acinar cell suspension, and then transferring 50 ul from each sample to another tube for analysis. These are termed "O value tubes."

The "total amylase" was determined by combining each of two 500 ul samples of acinar cell suspension in a tube with 5 ml of lysing solution (prepared by combining 1.0 ml of 100 mM CaCl$_2$, 1.45 g NaH$_2$PO$_4$, 0.1 g sodium dodecylsulfate, 0.1 g BSA (Fraction V) in 100 ml H$_2$O and adjusting pH to 7.8 with NaOH). The tube was covered with parafilm and vortexed vigorously. Then 150 ul of the solution was transferred to each of two other tubes.

From each of the incubated samples, 400 ul was removed to a microfuge tube and spun for 30 seconds at high speed on a tabletop centrifuge. Then, two 50 ul aliquots were transferred to different tubes (50 ul each); these are termed "experiment tubes."

Then 100 ul of lysing solution was added to each of the "O-value" tubes and each of the "experiment" tubes.

4 Phadebas Amylase Assay Tablets (Pharmacia, Inc., Piscataway, New Jersey, U.S.A.) were dissolved in 25 ml of amylase reagent buffer (100 mg NaN$_3$, 1.43 gm NaCl and 1.40 gm NaH$_2$PO$_4$ in 500 ml H$_2$O, pH is adjusted to 7.0 with NaOH). While the Phadebas solution was still stirring, 1.0 ml was taken and added to each of the O-value tubes and "experiment" tubes. The tubes were then incubated at 37° C. until color development occurred (approximately 15 minutes). (It was made certain that starch substrate for the assay did not become limiting.) When color had developed sufficiently that there was a clear difference between the "no VIP" experiment tubes and the experiment tubes with VIP, the reactions were stopped by adding to each tube 2.75 ml of 0.045M NaOH. Each sample was then centrifuged at 2200 × g for 5 minutes and the optical density of each sample was measured at 620 nm. The fraction of amylase released was then calculated as $$\frac{(O.D.)_{unknown} - (O.D.)_{\text{"O" tube}}}{[3.67 \times (O.D.)_{Total\ Amylase}] - (O.D.)_{\text{"O" tube}}},$$

where "O.D."$_{\text{"O" tube}}$ is the average O.D. of the "O" value tubes; "O.D."$_{total\ amylase}$ is the average O.D. of the "total amylase" tubes; and 3.67 is a dilution factor for the total amylase tubes. The average was determined of the fractions of amylase released from the "experiment tubes" for each concentration of analog, and this average was taken as the fraction released due to the analog at the involved concentration.

In plots of fraction of amylase released against logarithm of VIP analog concentration, it has been found that, for all analogs, the fraction released plateaus at about the same fraction. The "ED$_{50}$" for an analog was taken to be the concentration that caused a release of a half of the maximum released, (i.e., the plateau value). The "potency" of an analog, compared with naturally occurring human VIP (i.e., ED$_{50}$ for the human VIP standard divided by ED$_{50}$ for the analog) is a measure of the bioactivity of the analog relative to that of the standard. The results obtained were as follows:

| Analog | Potency (Amylase Release Assay) |
| --- | --- |
| Human VIP | 1.0 |
| Human VIP, non-amidated at carboxy terminus | 0.4 |
| Chicken VIP | 0.5 |
| Guinea Pig VIP | 0.05 |
| I | $5 \times 10^{-4}$ |
| II | $1 \times 10^{-4}$ |
| III | $1.0 \times 10^{-3}$ |
| IV | $4.4 \times 10^{-3}$ |
| V | 0.2 |
| VII | $1.0 \times 10^{-3}$ |
| IX | $7 \times 10^{-4}$ |

EXAMPLE IV

Analog Stability Against Proteolytic Degradation

The stability of naturally occurring, human VIP and various analogs described in Example I was assessed by determining their resistance to degradation when incubated with a crude rat-lung homogenate.

For the assay, the lungs were taken from a female Sprague-Dawley rat and were perfused with ice-cold phosphate-buffered saline, as described in Example II. The whitened lungs were polytroned and then homogenized in Degradation Assay Buffer (25 mM Tris, 5 mM MgCl$_2$, pH 7.4), and the homogenate was filtered through cheesecloth. The filtrate was then diluted to a final volume of 500 ml with Degradation Assay Buffer, to yield the crude lung homogenate.

Resistance to degradation was measured by determining the half-life of the human VIP or analog in the crude lung homogenate. To determine these half-lives, the human VIP or analog was added to 1 ml of the crude homogenate to a concentration of $10^{-5}$M, and the mixture was incubated at 37° C. After incubation for the desired time period, the sample was placed in a 100° C. bath and boiled for 5 minutes, and then acidified with glacial acetic acid (10% final volume) and, finally, cooled rapidly by being placed on dry ice. The sample was then microfuged at 4° C. for 15 minutes, and the supernatant analysized for peptide content by HPLC. Test reactions indicated that no decomposition products from the homogenate coeluted with the intact human VIP or any intact analog. The results, expressed as half-life of the intact human VIP or analog, are as follows:

| ANALOG | HALF-LIFE (minutes) |
| --- | --- |
| Human VIP | 16 |
| Chicken VIP | 15 |
| I | 4 |
| II | 7.5 |
| III | 4 |
| IV | 5 |
| V | 2.5 |

While the invention has been illustrated herein with some specificity, it will be obvious to those skilled in the art that various modifications and variations can be made in the specifics without departing from the spirit of the invention. Such modifications and variations are also within the scope of the invention as described and claimed herein.

What is claimed is:

1. A VIP analog of the formula: H-S-D-A-V-$X_{11}$-$X_{21}$-D-$X_{22}$-$X_{12}$-$X_{23}$-$X_{31}$-$X_{41}$-R-$X_{32}$-$X_{33}$-$X_{51}$-A-$X_{52}$-$X_{34}$-$X_{35}$-$X_{13}$-$X_{53}$-$X_{24}$-$X_{25}$-$X_{55}$-$X_{56}$-$X_{26}$-(NH$_2$)$_i$, wherein $X_{11}$, $X_{12}$, and $X_{13}$ are the same or different and are each selected from the group consisting of F and Y; $X_{21}$, $X_{22}$, $X_{23}$, $X_{24}$, $X_{25}$, and $X_{26}$ are the same or different and are each selected from the group consisting of T, S, Q, N, and A; $X_{31}$, $X_{32}$, $X_{34}$, and $X_{35}$ are the same or different and are each selected from the group consisting of R, K, S, and Q; $X_{33}$ is selected from the group consisting of R, K and S; $X_{41}$ is selected from the group consisting of L, M, V, I, F, and Y; $X_{51}$, $X_{52}$, $X_{53}$, and $X_{55}$ are the same or different and are each selected from the group consisting of L, M, I, and V; and $X_{56}$ is selected from the group consisting of L and V; and wherein i is 0 or 1, wherein 0 indicates that the peptide is not carboxy-terminal-amidated and 1 indicates that the peptide is carboxy-terminal-amidated; or a pharmaceutically acceptable salt of the analog.

2. An analog according to claim 1 with the formula:
H-S-D-A-V-Y-S-D-S-F-S-R-Y-R-R-S-V-A-L-R-R-F-V-S-N-V-V-T-(NH $_2$) or a pharmaceutically acceptable salt thereof.

3. An analog according to claim 1 with the formula:
H-S-D-A-V-Y-S-D-S-F-S-R-Y-R-S-R-V-A-L-S-R-F-V-R-N-V-V-T-(NH $_2$) or a pharmaceutically acceptable salt thereof.

4. An analog according to claim 1 with the formula:
H-S-D-A-V-Y-S-D-S-F-R-S-Y-R-S-R-V-A-L-S-R-F-V-R-N-V-V-T-(NH $_2$) or a pharmaceutically acceptable salt thereof.

5. An analog according to claim 1 with the formula:
H-S-D-A-V-F-S-D-S-Y-S-R-F-R-R-S-M-A-V-R-R-Y-L-S-N-V-L-T-(NH $_2$) or a pharmaceutically acceptable salt thereof.

6. An analog according to claim 1 with the formula:
H-S-D-A-V-F-T-D-N-Y-S-R-F-R-K-S-V-A-V-K-K-Y-L-N-S-V-L-T-(NH $_2$) or a pharmaceutically acceptable salt thereof.

7. A VIP analog selected from the group consisting of those of formulae:
H-S-D-A-V-Y-T-D-N-F-S-R-Y-R-K-Q-V-A-L-K-K-F-V-N-S-V-V-T-(NH $_2$)$_i$,
H-S-D-A-V-Y-S-D-S-F-S-R-F-R-K-Q-M-A-V-K-K-Y-L-N-S-V-L-T-(NH $_2$)$_i$,
H-S-D-A-V-F-T-D-N-Y-S-R-Y-R-R-Q-M-A-V-K-K-Y-L-N-S-V-L-T-(NH $_2$)$_i$,
H-S-D-A-V-F-T-D-N-Y-S-R-F-R-K-Q-M-A-V-R-R-F-V-N-S-V-L-T-(NH $_2$)$_i$, and
H-S-D-A-V-F-T-D-N-Y-S-R-F-R-K-Q-M-A-V-K-K-Y-L-S-N-V-V-T-(NH $_2$)$_i$,
wherein i is 0 or 1, wherein 0 indicates that the peptide is not carboxy-terminal-amidated and the 1 indicates that the peptide is carobxy-terminal-amidated; or a pharmaceutically acceptable salt of the analog.

8. An analog according to claim 7 with the formula:
H-S-D-A-V-Y-T-D-N-F-S-R-Y-R-K-Q-V-A-L-K-K-F-V-N-S-V-V-T-(NH $_2$) or a pharmaceutically acceptable salt thereof.

9. An analog according to claim 7 with the formula:
H-S-D-A-V-Y-S-D-S-F-S-R-F-R-K-Q-M-A-V-K-K-Y-L-N-S-V-L-T-(NH $_2$) or a pharmaceutically acceptable salt thereof.

10. An analog according to claim 7 with the formula:
H-S-D-A-V-F-T-D-N-Y-S-R-Y-R-R-Q-M-A-V-K-K-Y-L-N-S-V-L-T-(NH $_2$) or a pharmaceutically acceptable salt thereof.

11. An analog according to claim 7 with the formula:
H-S-D-A-V-F-T-D-N-Y-S-R-F-R-K-Q-M-A-V-R-R-F-V-N-S-V-L-T-(NH $_2$) or a pharmaceutically acceptable salt thereof.

12. An analog according to claim 7 with the formula:
H-S-D-A-V-F-T-D-N-Y-S-R-F-R-K-Q-M-A-V-K-K-Y-L-S-N-V-V-T-(NH $_2$) or a pharmaceutically acceptable salt thereof.

* * * * *

UNITED STATES PATENT AND TRADEMARK OFFICE
CERTIFICATE OF CORRECTION

PATENT NO. : 4,835,252

DATED : May 30, 1989

INVENTOR(S) : Musso et al.

It is certified that error appears in the above-identified patent and that said Letters Patent is hereby corrected as shown below:

| | |
|---|---|
| Column 2, Line 17: | Change "recombiannt" to --recombinant--. |
| Column 2, Line 68: | Change "harmone's" to --hormone's--. |
| Column 3, Line 27: | Between "V-" and "$X_{21}$-" add --$X_{11}$---. |
| Column 3, Line 27: | Delete the space between "$X_{22}$" and "-$X_{12}$". |
| Column 3, Line 30: | After "different" insert --and--. |
| Column 4, Line 62: | Change "4689,318" to --4,689,318--. |
| Column 4, Line 62: | Delete "and". |
| Column 8, Line 3: | After "50-250" insert --mg--. |
| Column 9, Line 36: | Before "Synthesis" insert --(c)--. |
| Column 9, Line 40: | Between "R-R-" and "M-A-" insert --S---. |
| Column 10, Line 18: | Change "(b)" to --(d)--. |
| Column 10, Line 19: | Change "Analog" to --Analogs--. |
| Column 15, Line 35: | Change "$X_{21}$-" to --$X_{21}$--- |

UNITED STATES PATENT AND TRADEMARK OFFICE
CERTIFICATE OF CORRECTION

PATENT NO. : 4,835,252

DATED : May 30, 1989

INVENTOR(S) : Musso et al.

It is certified that error appears in the above-identified patent and that said Letters Patent is hereby corrected as shown below:

Column 16, Line 2:   Change "$(NH\ _2)$" to --$(NH_2)$--.

Column 16, Line 6:   Change "$(NH\ _2)$" to --$(NH_2)$--.

Column 16, Line 10:  Change "$(NH\ _2)$" to --$(NH_2)$--.

Column 16, Line 14:  Change "$(NH\ _2)$" to --$(NH_2)$--.

Column 16, Line 18:  Change "$(NH\ _2)$" to --$(NH_2)$--.

Column 16, Line 23:  Change "$(NH\ _2)$" to --$(NH_2)$--.

Column 16, Line 25:  Change "$(NH\ _2)$" to --$(NH_2)$--.

Column 16, Line 27:  Change "$(NH\ _2)$" to --$(NH_2)$--.

Column 16, Line 29:  Change "$(NH\ _2)$" to --$(NH_2)$--.

Column 16, Line 31:  Change "$(NH\ _2)$" to --$(NH_2)$--.

Column 16, Line 38:  Change "$(NH\ _2)$" to --$(NH_2)$--.

Column 16, Line 42:  Change "$(NH\ _2)$" to --$(NH_2)$--.

Column 16, Line 46:  Change "$(NH\ _2)$" to --$(NH_2)$--.

UNITED STATES PATENT AND TRADEMARK OFFICE
CERTIFICATE OF CORRECTION

PATENT NO. : 4,835,252

DATED : May 30, 1989

INVENTOR(S) : Musso et al.

It is certified that error appears in the above-identified patent and that said Letters Patent is hereby corrected as shown below:

Column 16, Line 50:   Change "$(NH_2)$" to --$(NH_2)$--.

Column 16, Line 54:   Change "$(NH_2)$" to --$(NH_2)$--.

Signed and Sealed this

Tenth Day of April, 1990

Attest:

HARRY F. MANBECK, JR.

*Attesting Officer*　　　　　*Commissioner of Patents and Trademarks*